United States Patent
Norton

(10) Patent No.: US 12,042,414 B2
(45) Date of Patent: Jul. 23, 2024

(54) SPLINT DEVICE

(71) Applicant: Sean C. Norton, Kyle, TX (US)

(72) Inventor: Sean C. Norton, Kyle, TX (US)

(*) Notice: Subject to any disclaimer, the term of this patent is extended or adjusted under 35 U.S.C. 154(b) by 895 days.

(21) Appl. No.: 17/041,242

(22) PCT Filed: Mar. 27, 2019

(86) PCT No.: PCT/US2019/024310
§ 371 (c)(1),
(2) Date: Sep. 24, 2020

(87) PCT Pub. No.: WO2019/191248
PCT Pub. Date: Oct. 3, 2019

(65) Prior Publication Data
US 2021/0106449 A1     Apr. 15, 2021

Related U.S. Application Data

(60) Provisional application No. 62/648,803, filed on Mar. 27, 2018.

(51) Int. Cl.
*A61F 5/00* (2006.01)
*A61F 5/01* (2006.01)

(52) U.S. Cl.
CPC ............ *A61F 5/0102* (2013.01); *A61F 5/013* (2013.01)

(58) Field of Classification Search
CPC .................................................... A61F 5/0127
See application file for complete search history.

(56) References Cited

U.S. PATENT DOCUMENTS 1,381,290 A * 6/1921 Diadul, Jr. ............ A61F 5/0127
                                                              602/27
2,138,975 A * 12/1938 Malik ................. A61F 5/05841
                                                              602/16
(Continued)

FOREIGN PATENT DOCUMENTS

JP         2018-000585 A      1/2018

OTHER PUBLICATIONS

International Search Report issued in International Application No. PCT/US2019/024310, dated Mar. 27, 2018, 9 pages.

*Primary Examiner* — Kim M Lewis
(74) *Attorney, Agent, or Firm* — Denise L. Mayfield; DYKEMA GOSSETT P.L.L.C.

(57) ABSTRACT

A splint device for stabilizing and/or securing a limb or appendage in a fixed position is provided. The splint device can include a first plate member and a second plate member connected together at one end by a hinged connection member. The hinged connection member can be configured to allow each plate member to be rotated relative to one another and selectively locked into a fixed position. The splint device can include a third plate member connected to the second plate member by a second hinged connection. The rotation of each plate member relative to the other can allow the splint device to be selectively positioned in a fixed configuration to generally match the shape and contour of a limb or appendage in a desired configuration. The splint device permits the accommodation of a joint (elbow, wrist, knee, ankle), and may provide for multiple configurations at a splinted limb.

18 Claims, 21 Drawing Sheets

(56) References Cited

U.S. PATENT DOCUMENTS

| | | | | |
|---|---|---|---|---|
| 4,280,490 A * | 7/1981 | Santy | ............... | A61F 5/05883 |
| | | | | 602/16 |
| 6,080,122 A | 6/2000 | Gulledge | | |
| 6,293,918 B1 * | 9/2001 | Wang | ............... | A61F 5/05858 |
| | | | | 128/881 |
| 7,552,733 B1 * | 6/2009 | Schubert, III | ......... | A47C 16/00 |
| | | | | 5/607 |
| 7,704,218 B2 * | 4/2010 | Einarsson | ............. | A61F 5/0125 |
| | | | | 602/5 |
| 8,979,781 B2 * | 3/2015 | Cook | ............... | A61F 5/05825 |
| | | | | 602/5 |
| D829,331 S * | 9/2018 | Norton | ....................... | D24/231 |
| 2005/0145255 A1 | 7/2005 | Mengato | | |
| 2006/0155233 A1 | 7/2006 | Huber et al. | | |
| 2008/0200855 A1 | 8/2008 | Pomeroy et al. | | |
| 2008/0234614 A1 * | 9/2008 | Patel | ............... | A61F 5/05841 |
| | | | | 602/5 |
| 2010/0016772 A1 * | 1/2010 | DeToro | ............... | A61F 5/0125 |
| | | | | 602/26 |
| 2010/0130900 A1 | 5/2010 | Detoro et al. | | |
| 2017/0216078 A1 * | 8/2017 | Rivlin | ............... | A61F 5/05866 |
| 2017/0231794 A1 | 8/2017 | Church | | |

\* cited by examiner

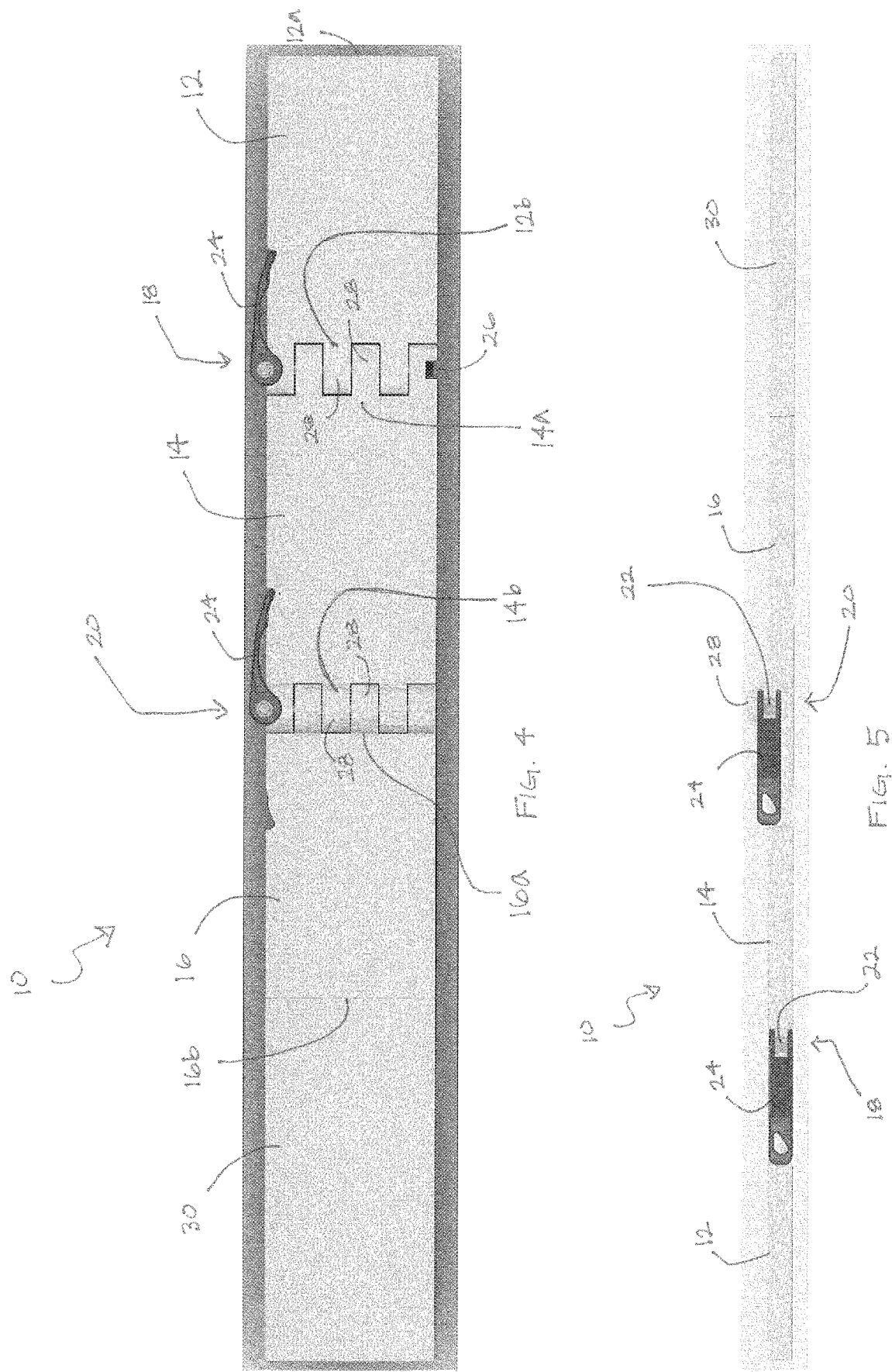

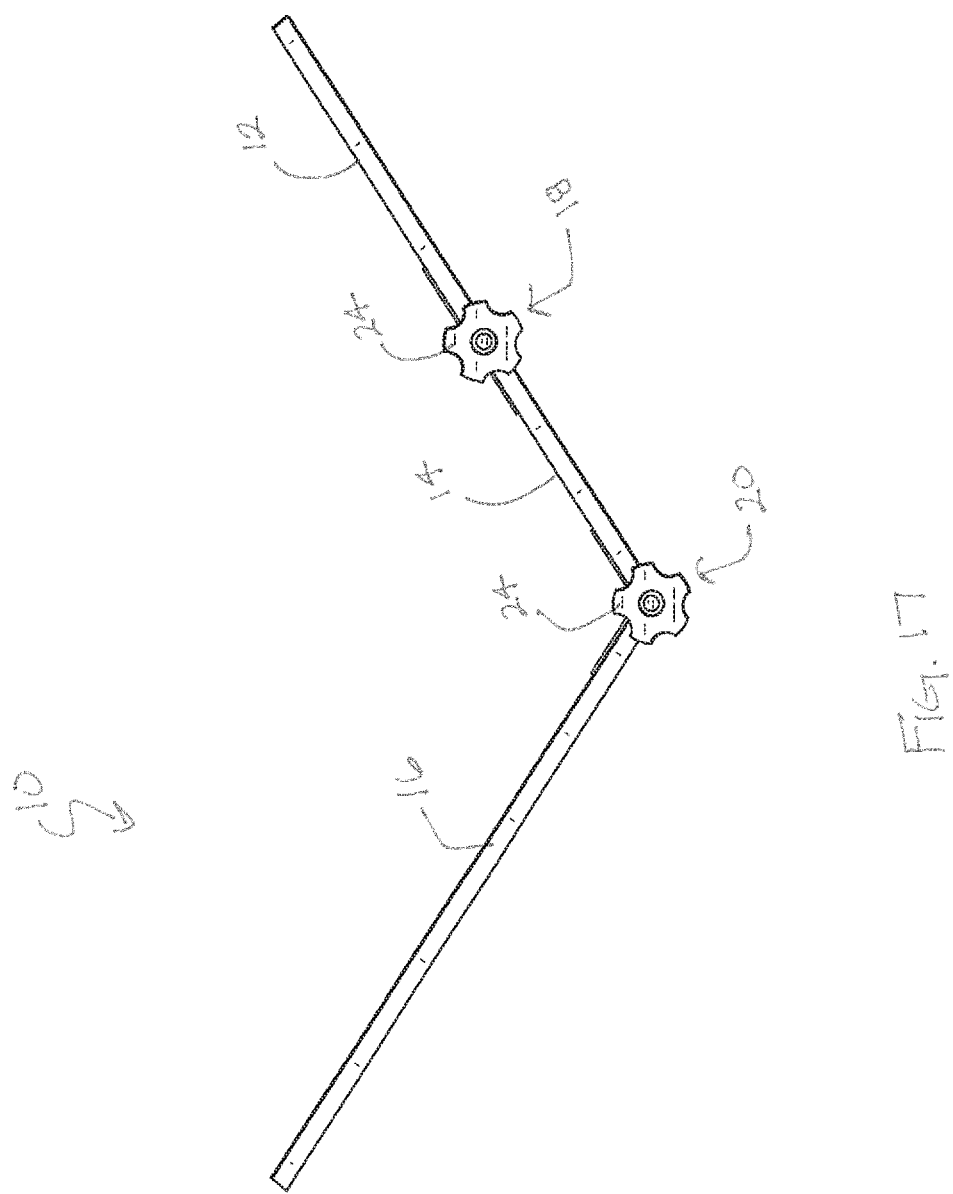

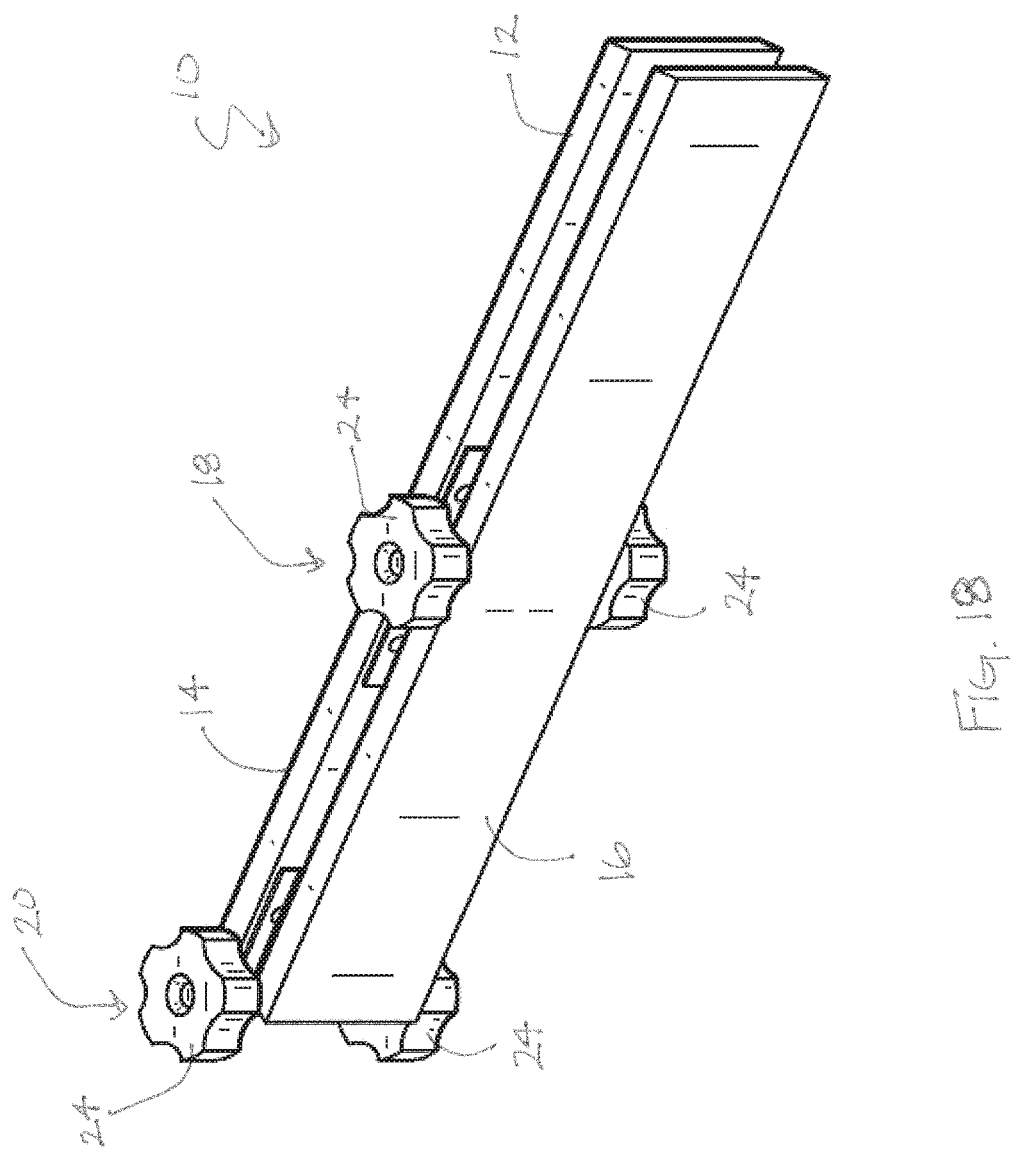

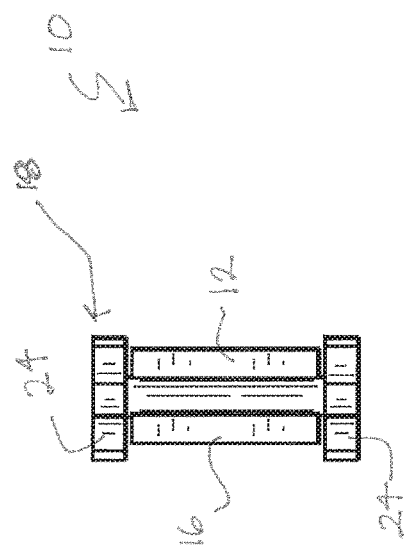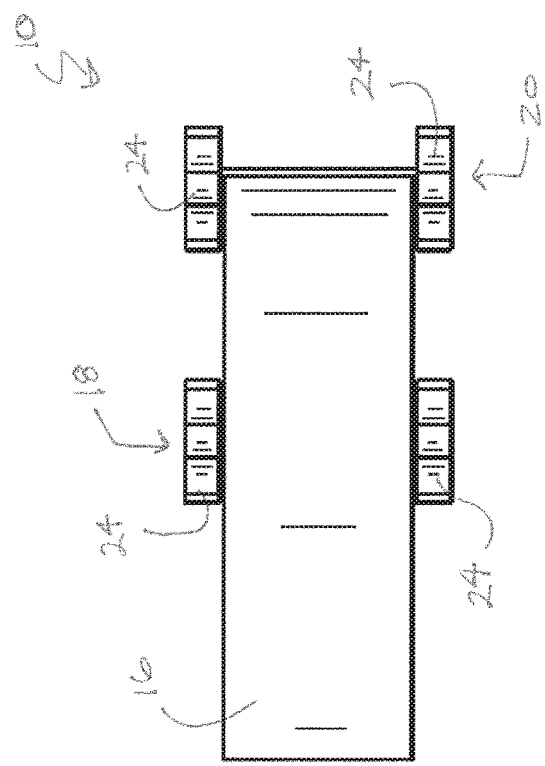

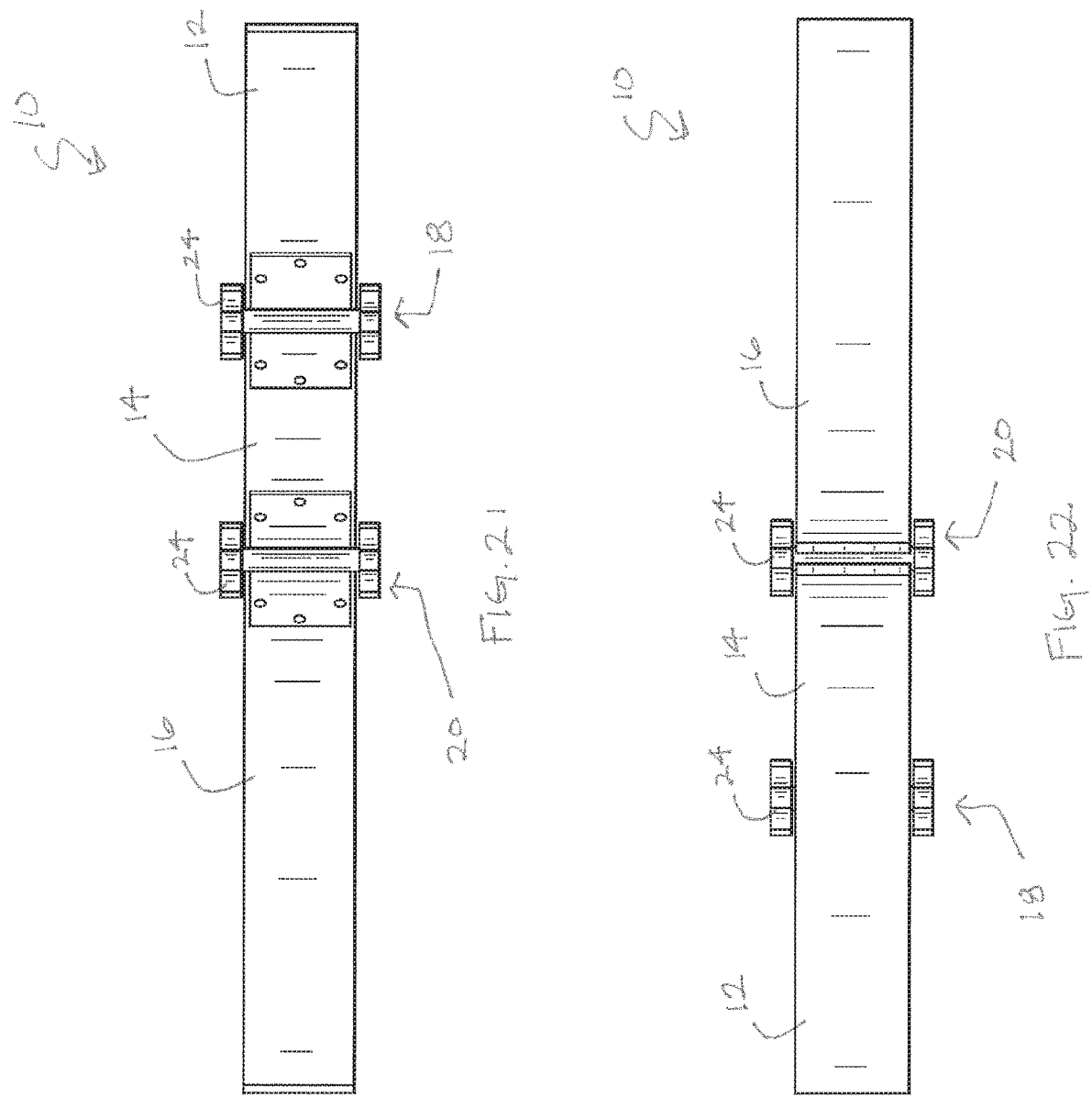

SPLINT DEVICE

CROSS-REFERENCE TO RELATED APPLICATIONS

This Application claims priority to U.S. Provisional Patent Application Ser. No. 62/648,803, filed on Mar. 27, 2018, to Sean C. Norton, entitled "Splint Device," the entire disclosure of which is incorporated herein by reference.

BACKGROUND OF THE INVENTION

Medical splint devices are commonly used to stabilize an injured limb during a medical emergency and/or in connection with orthopedic rehabilitation. Splint devices commonly known in the art typically include an elongated, rigid board or foam member that is placed against an injured limb. With a foam member, an aluminum strip is typically employed to provide stability and/or flexibility to the foam member. A strap or surgical wrap, such as an elastic bandage, may be wrapped around the board member or foam member and the limb once the splint has been placed in order to maintain the limb in a fixed position, or to at least limit movement until a more permanent solution may be obtained.

One type of splinting device is a rollable and foldable foam strip splint, such as the SAM® Splint. The SAM® Splint comprises an elongated strip of aluminum material covered by a foam member on each side. Another type of splinting device is a padded board splint, such as the MORRISON SPLINT™. The MORRISON SPLINT provides a flattened elongated wooden board with a foam padding layer on one side. Yet another type of splinting device is a cardboard splint, for example, the cardboard splint provided by FERNO®. This cardboard splint provides a flat piece of cardboard with an elongated center strip and two foldable wings on each side. An arm or leg may be placed along the elongated center, and the wings on each side folded over the arm or leg. The wings also include openings to accommodate ties that hold the wings in a folded configuration on the extremity.

One problem with these methods/types of splitting techniques/devices is that they do not adequately conform to the shape/contours of an arm/leg, at least in part because of the immobility/rigidity of the flattened board and/or foam member of the device. Additionally, in many cases the technique/device does not accommodate a joint (elbow, wrist, knee, ankle) of the limb, thus further compromising fit at the appendage. A further observed limitation includes a limited amount of conformability of the splinting device that precludes appropriate splinting of an injured/rehabilitating limb requiring multiple splinting configurations.

Another type of splinting device commonly known in the art is a wire ladder splint, such as the Ladder Splint provided by FERNO®. These types of splints comprise an elongated metal wire strip with a plurality of cross-bars that form a ladder-shaped structure. The wire structure allows the splint to be bent and/or folded at one or more sections along its length in order to conform to a desired shape. The splint can then be applied to an extremity and secured using bandages, straps, tape, ties or the like. These ladder splints are difficult to fold accurately and do not lend to multiple folds or bends across the length of the splint. In addition, because the wire structure is designed to be folded by hand, they lack sufficient rigidity necessary to adequately and safely secure an appendage in a fixed position (as the bends formed into the wire structure can be manipulated with relatively little force). Finally, these wire ladder splints are generally not suitable for reuse because the any folds/bends placed into the wire structure weaken the strength of the splint after use.

A need continues to exist in the medical arts for a splinting device and for techniques for splinting that avoid, or at least reduce, the foregoing problems, while providing an economical, efficient and easy-to-use splinting tool suitable for stabilizing a limb, especially a limb having an injury in an emergency situation.

SUMMARY OF THE INVENTION

The present invention relates generally to a splint device configured for assisting in stabilizing and/or securing an arm, leg or other appendage or part thereof, in a relatively secured position.

In a general and overall sense, the present invention provides a splinting device that is lightweight, multi-functional and flexible.

In one aspect, the splint device comprises at least two plates and a hinged connection. In another aspect, the splint device comprises at least three plates and two hinged connections.

According to one embodiment, the splint device comprises a first plate member having a free end and a connected end, a second plate member having a first connected end and a second connected end, and a first hinged connection member configured to connect the first and second plate members together, wherein the first hinged connection member allows the first and second plate members to be selectively rotated relative to one another.

According to one embodiment, the splint device can include a plurality of knuckles provided at the connected ends of each plate member to allow the ends to be interconnected together at the first hinged connection.

According to one embodiment, the hinged connection member can comprise a pin, a fastener and a cam lever.

According to one embodiment, the connected ends of each of the plate members can include a slot configured to allow the pin of the hinged connection member to be inserted through the slot.

According to one embodiment, the first plate member can be configured to be rotated relative to the second plate member by at least 180 degrees about an axis extending longitudinally though the hinged connection member.

According to one embodiment, the plate members are formed by a three-dimensional printing process.

According to one embodiment, the plate members are formed by an injection molding method.

According to one embodiment, the plate members can have a structural pattern formed into at least one surface of the plate members. The structural pattern can be configured to reduce overall mass of each plate member and the splint device overall, while still maintaining sufficient structural rigidity and strength to prevent undesired flexing and bending of the plate members.

According to one embodiment, the structural pattern can also be configured with one or more sockets or receptacles that are designed to attach and hold accessories to the splint device, such as straps or additional parts. The sockets or receptacles in the structural pattern may be designed and configured to substantially correspond to connection components provided with such accessories for the splint device.

According to one embodiment, the structural pattern comprises a honeycomb or hexagonal-shaped pattern structure.

According to one embodiment, the splint device can include a first plate member, a second plate member and an extension plate member.

According to one embodiment, the splint device can comprise a first plate member, a second plate member, a third plate member, a first hinged connection member connecting the first and second plate members, and a second hinged connection member connecting the second and third plate members together.

According to one embodiment, the splint device can comprise a first plate member, a second plate member, a third plate member, a first hinged connection member connecting the first and second plate members, and a second hinged connection member connecting the second and third plate members together.

According to one embodiment, the third plate member may be rotated relative to the second plate member by at least 180 degrees about an axis extending longitudinally through the second hinged connection member.

According to one embodiment, the extension plate of the splint device can be fixedly connected to a free end of the third plate member.

The splint device can designed to be flexible and conformable to the subject on which it is provided, and in this manner provides an advantage over prior emergency use split devices that are essentially immovable. The splint device can also be enabled to accurately conform to the contours and curvature of the subject to properly secure an arm, leg or other appendage of the subject in a fixed position. The splint device can also be configured to provide sufficient strength at the joints or bends created at the hinged connections as a result of the strength of the locking means and hinged connection members to provide an advantage over prior splint devices that allow for folding along the length of the splint.

Other aspects and advantages of the present invention will be apparent from the following detailed description of the preferred embodiments of the accompanying drawing figures.

DESCRIPTION OF THE SEVERAL VIEWS OF THE DRAWINGS

In the accompanying drawing, which forms a part of the specification and is to be read in conjunction therewith in which like reference numerals are used to indicate like or similar parts in the various views:

FIG. 4 is a top plan view of the medical splint device of FIG. 1;

FIG. 5 is a front elevation view of the medical splint device of FIG. 1;

FIG. 16 is a perspective view of a medical splint device in accordance with a fourth embodiment of the present invention;

FIG. 17 is an elevation view of the medical splint device of FIG. 16;

FIG. 18 is a perspective view of the medical splint device of FIG. 16 illustrating the device in a folded configuration;

FIG. 19 is an elevation view of the medical splint device of FIG. 16 illustrating the device in a folded configuration;

FIG. 20 is a plan view of the medical splint device of FIG. 16 illustrating the device in a folded configuration;

FIG. 21 is a bottom plan view of the medical splint device of FIG. 16;

FIG. 22 is a top plan view of the medical splint device of FIG. 16;

DETAILED DESCRIPTION OF THE INVENTION

Figure 1:
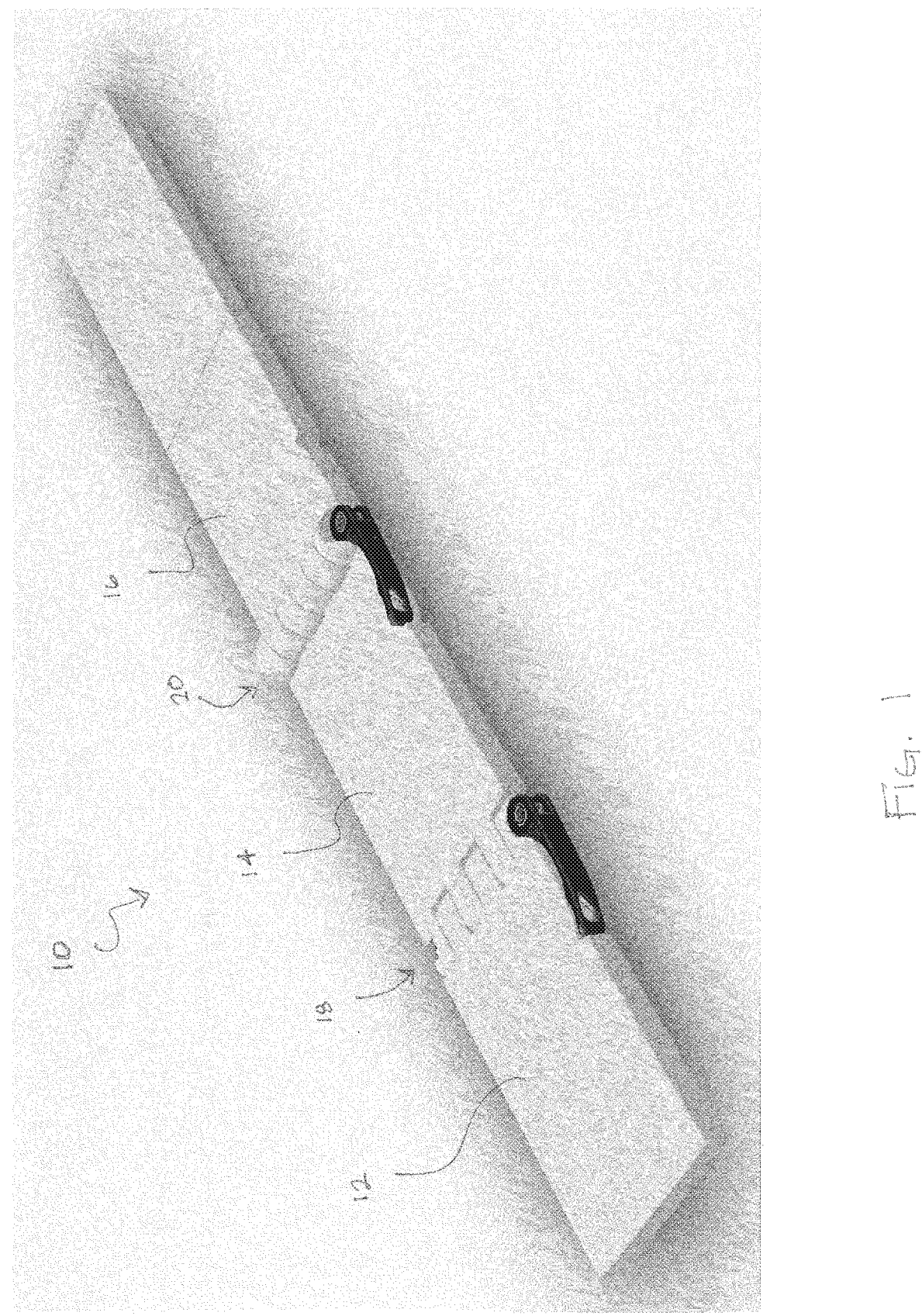
FIG. 1 is a front perspective view of a medical splint device in accordance with one embodiment of the present invention.
Figure 2:
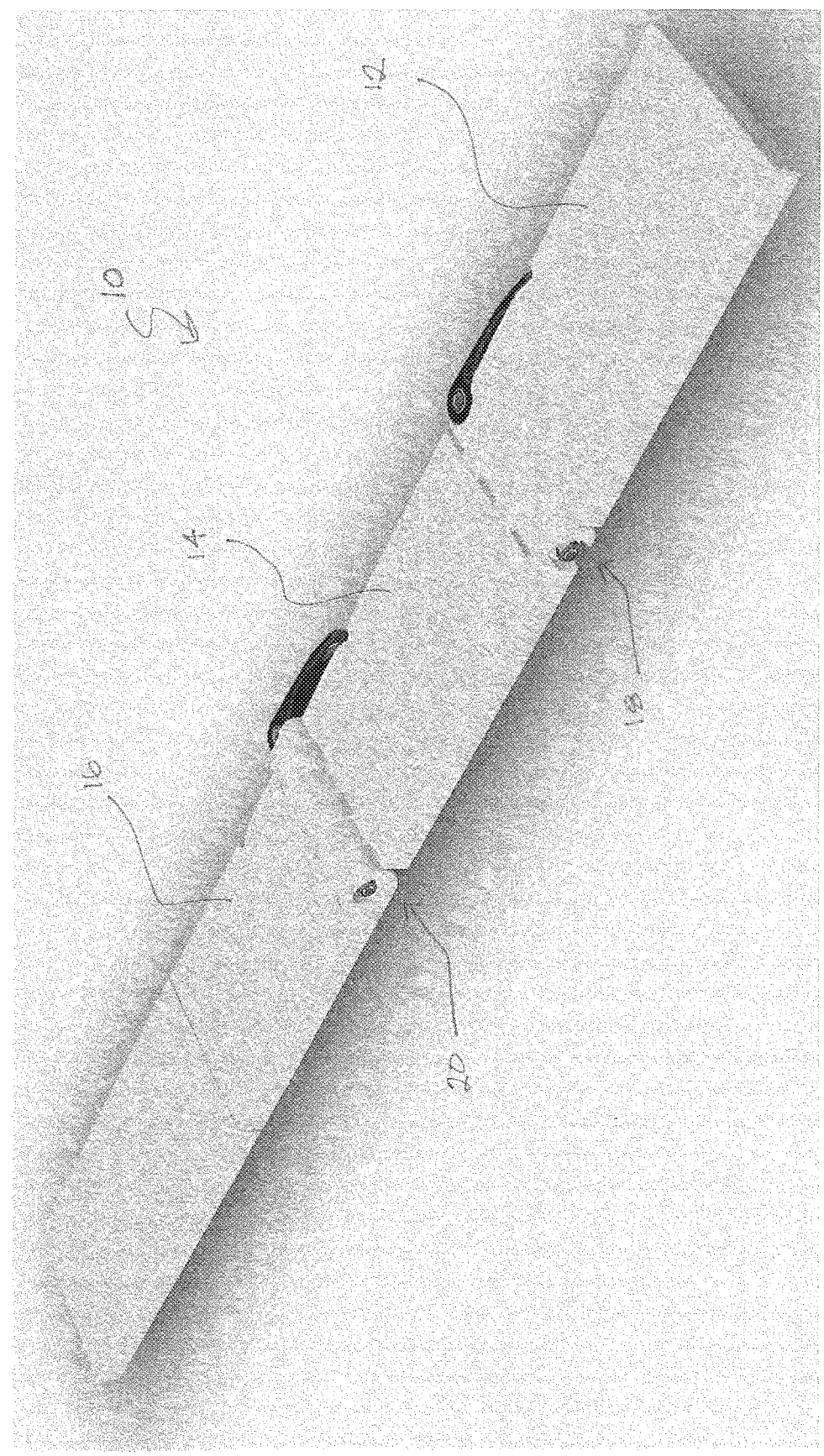
FIG. 2 is a rear perspective view of the medical splint device of FIG. 1.

The invention will now be described with reference to the drawing figures, in which like reference numerals refer to like parts throughout. For purposes of clarity in illustrating the characteristics of the present invention, proportional relationships of the elements have not necessarily been maintained in the drawing figures.

The following detailed description of the invention references specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The present invention is defined by the appended claims and the description is, therefore, not to be taken in a limiting sense and shall not limit the scope of equivalents to which such claims are entitled.

As illustrated in the several figures, the present invention is directed toward an emergency or medical splint device 10 configured to selectively secure a person's arm, leg, other appendage or appendages, or entire or portions of a body, in a fixed position following a medical injury or during rehabilitation therapy. As best shown in FIGS. 1-7, splint device 10, in accordance with one embodiment of the present invention, can include multiple plate members, such as three plate members 12, 14 and 16, and multiple hinged members, such as two hinged connection members 18 and 20, connecting the plate members 12, 14 and 16, together at their ends. The hinged connection members 18 and 20, can enable the splint device 10 to generally conform to the overall shape of a limb (e.g., arm or leg) by allowing the plate members 12, 14 and 16, to be selectively orientated relative to one another and then fixed in place to accommodate the limb. As described in greater detail below, plate members 12, 14 and 16, can be selectively rotated relative to one another about hinged connection members 18 and 20, to place splint device 10 in a desired shape and configuration (such as to match the shape of an injured limb), and then the hinged connection members 18 and 20, can be placed into a secured position to lock the plate members 12, 14 and 16, in place and provide splint device 10 as a rigid splint.

Figure 8:
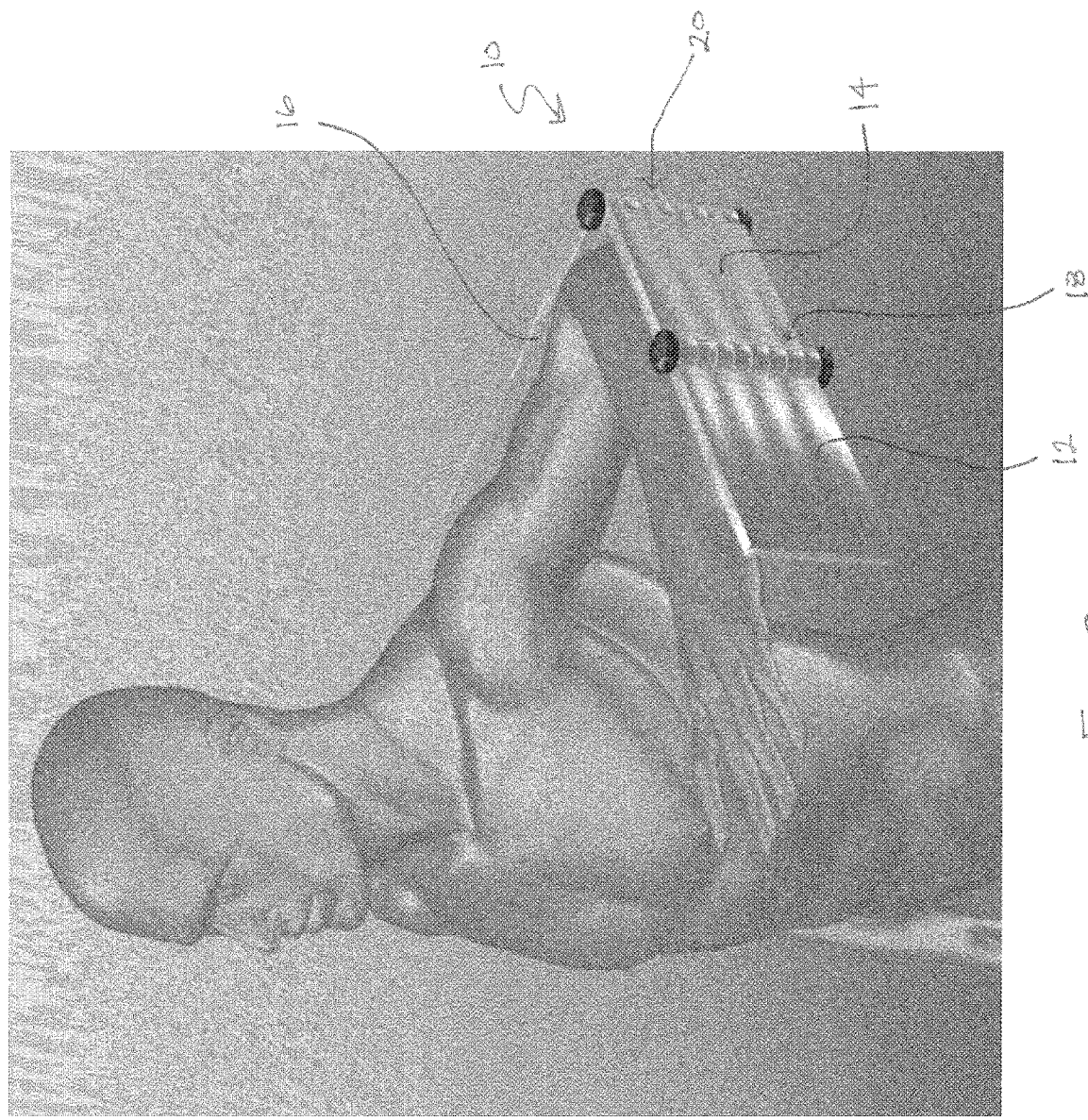
FIG. 8 is a schematic perspective view of a medical splint device positioned on a person's arm in accordance with one embodiment of the present invention.
Figure 9:
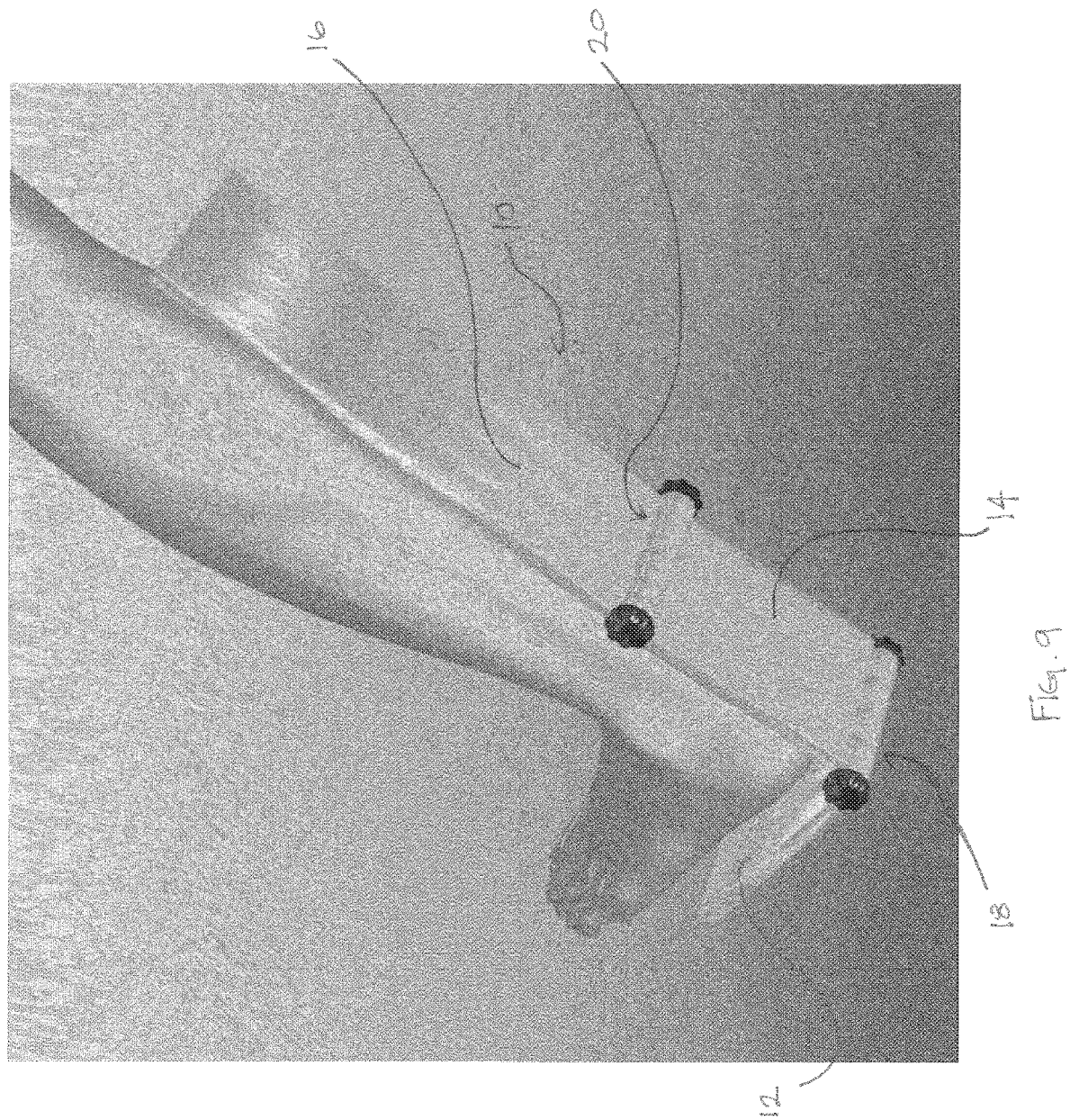
FIG. 9 is a schematic perspective view of a medical splint device positioned on a user's leg in accordance with one embodiment of the present invention.
Figure 26:
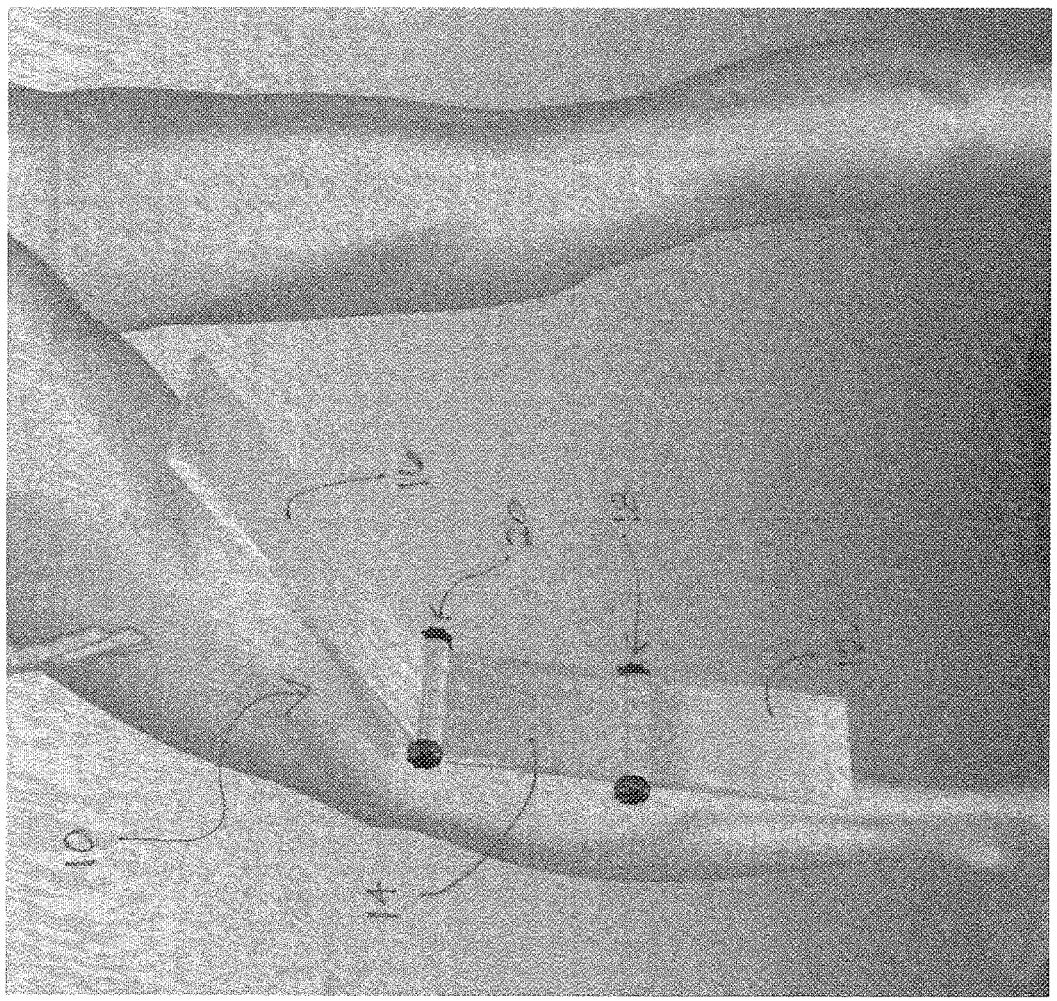
FIG. 26 is a schematic perspective view of a medical splint device positioned on a user's leg in accordance with one embodiment of the present invention.
Figure 27:
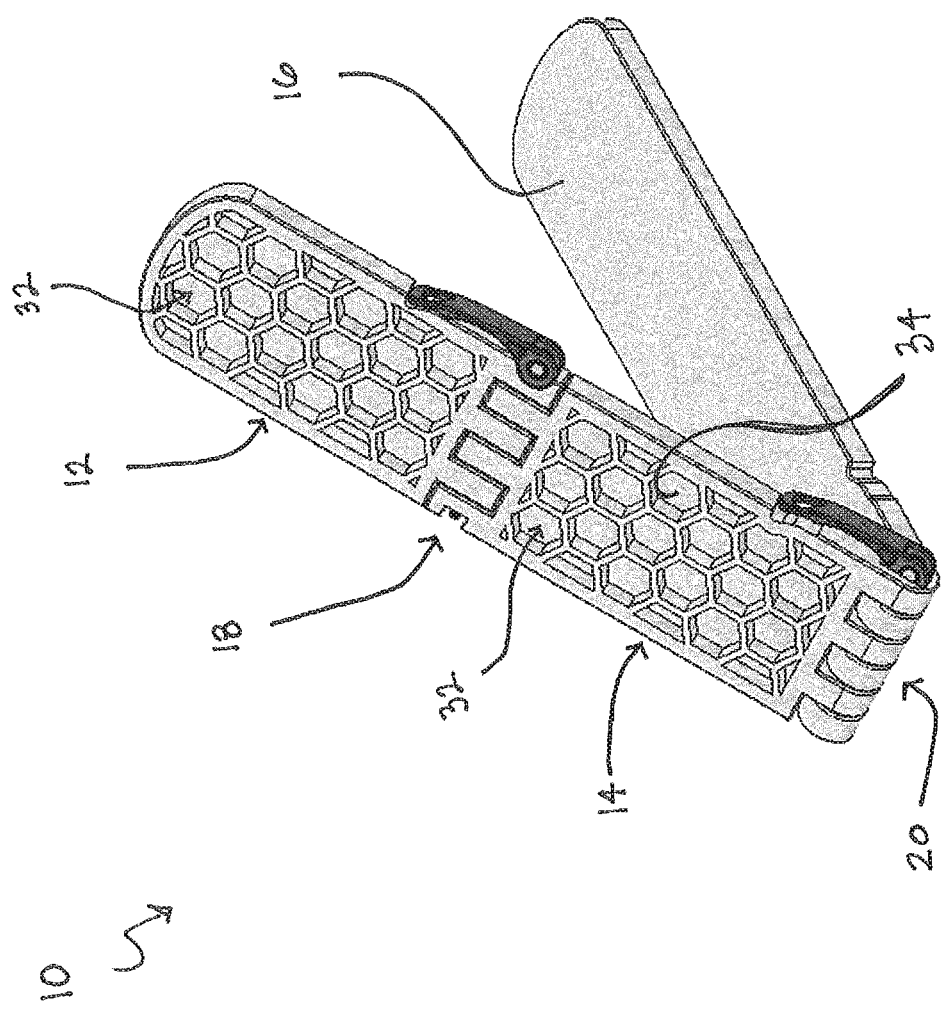
FIG. 27 is a perspective view of a medical splint device in accordance with a fifth embodiment of the present invention.
Figure 28:
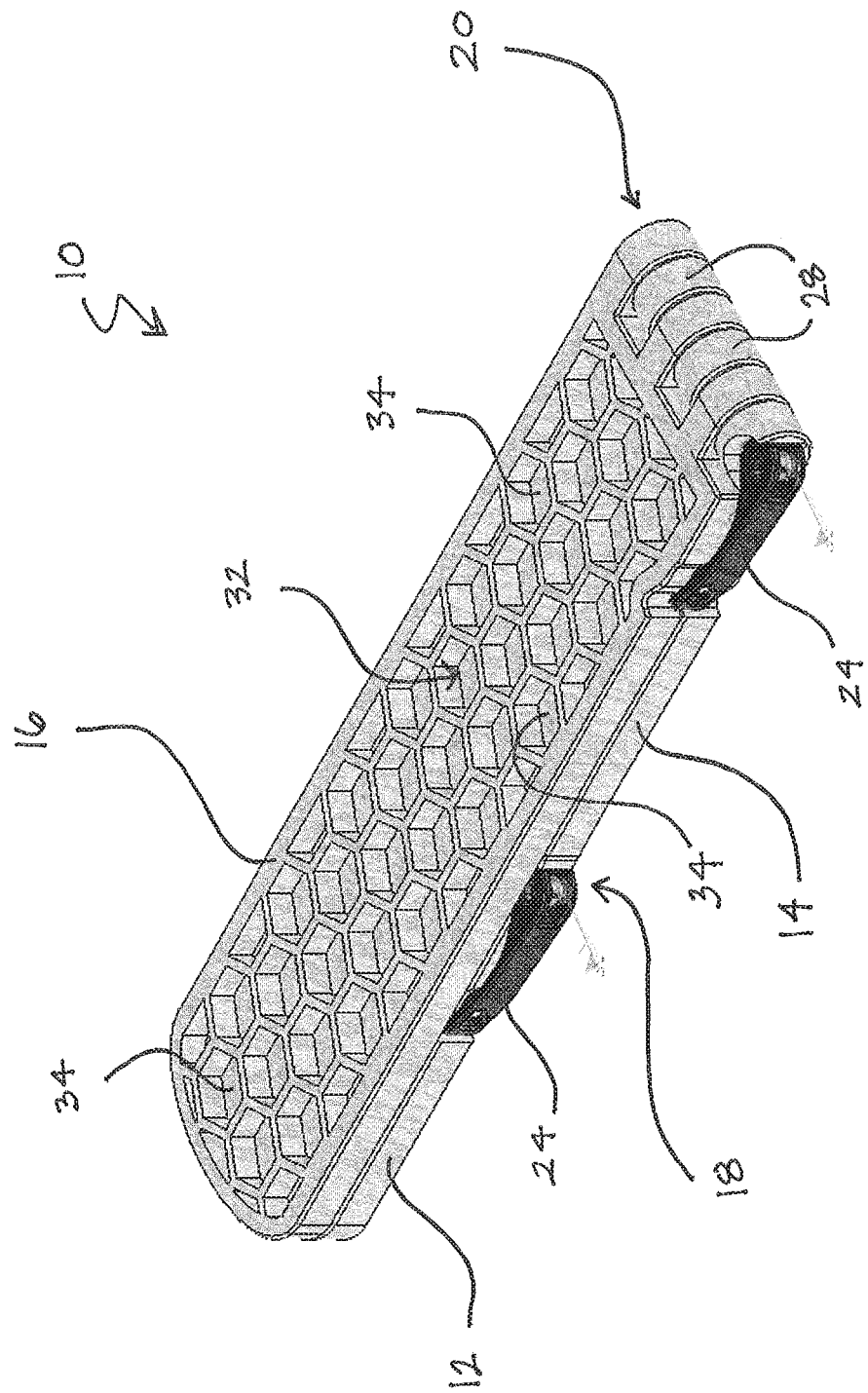
FIG. 28 is a perspective view of the medical splint device of FIG. 27 illustrating the device in a folded configuration.
Figure 29:
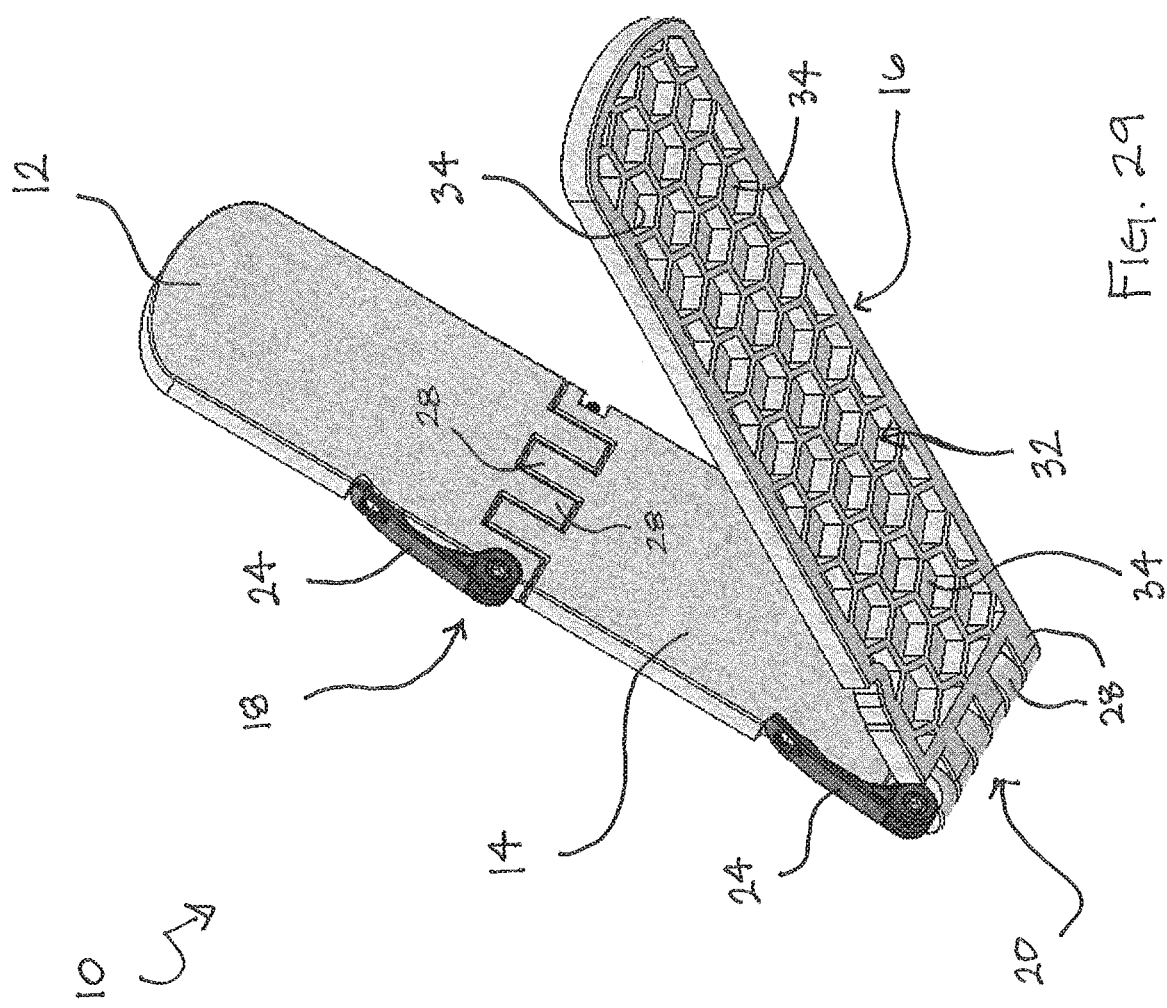
FIG. 29 is a perspective view of the medical splint device of FIG. 27.
Figure 30:
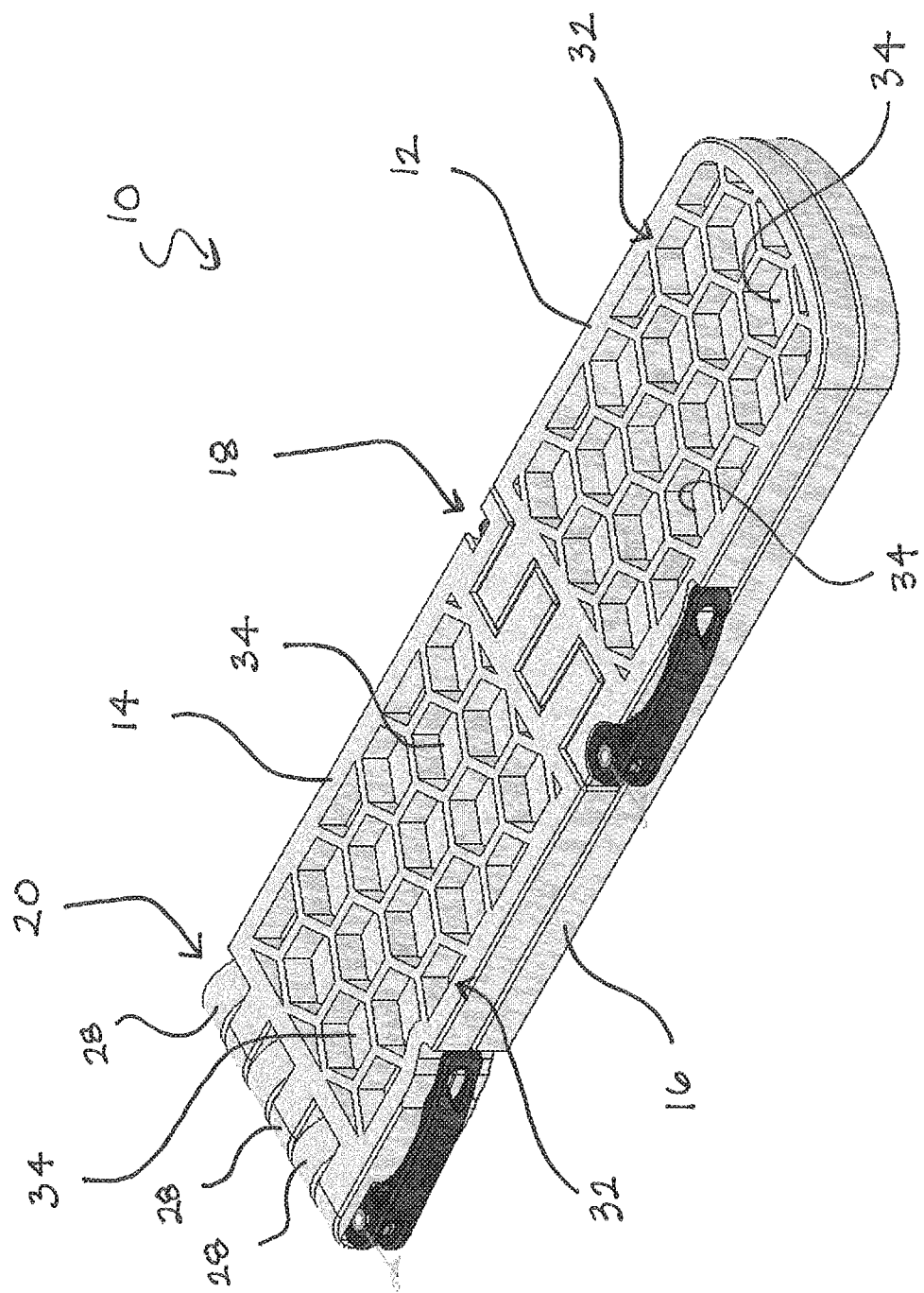
FIG. 30 is a perspective view of the medical splint device of FIG. 27 illustrating the device in a folded configuration.

As best shown in FIGS. 8-9 and 26, splint device 10 can be used to secure a person's limb in a selected position, particularly about a joint (such as an elbow, wrist, knee or ankle) in order to stabilize the limb and prevent undesired movement of the limb. While not shown in the figures, it is recognized that splint device 10 can be secured the applied limb using any suitable method, such as bandages, straps, tape, bands, or ties, which may be configured as part of splint device 10 or separately applied depending on the particular embodiment of the present invention. As further shown in FIGS. 8-9 and 26, the use of multiple hinged connections 18 and 20 can enable splint device 10 to more suitably conform to the individual shape and contours of a person's limb apart from the joint (such as the forearm or lower leg) to better stabilize the limb in a fixed position.

As best shown in FIGS. 1-7, according to one embodiment of the present invention, splint device 10 can include a first plate member 12, a second plate member 14 and a third plate member 16. Each plate member 12, 14 and 16 can be configured as a flattened, elongated plate, slat, board or member that can span across at least a portion of a person's limb. Depending on the particular embodiment, the plate members 12, 14 and 16 can be shaped and formed for generally fit the shape and configuration of at least a portion a person's limb. For example, one or the plate members 12, 14 and 16 may be configuration to match the curvature of a person's arm, forearm, etc. in order to provide a more conforming fit when splint device 10 is applied to an injured limb. Plate members 12, 14 and 16 can also be formed with different shapes and configurations or identical shapes and configurations depending on the particular embodiment of the present invention. Additionally, the plate members 12, 14 and 16 can be constructed from any suitable material, including without limitation, a plastic or polymer-based material, a metal, wood, foam, rubber or composite material, or any combination thereof. Plate members 12, 14 and 16 can further be constructed using any suitable construction techniques, including without limitation, 3-dimensional printing, injection molding or other suitable technique.

According to one embodiment of the present invention, as illustrated in FIGS. 27-30, one or more of plate members 12, 14 and 16 can include a structurally shaped pattern 32 formed into one or both of the surfaces of plate members 12, 14 and 16. As shown in FIGS. 27-30, according to one embodiment, structural pattern 32 is formed only on the bottom surface of the plate members 12, 14 and 16 while providing a uniform surface on the opposing side to comfortably receive a person's limb. As shown in FIGS. 27-30, pattern 32 can be defined into the surface of the plate member 12, 14 and 16 in the form of a honeycomb shaped pattern, hexagon-shaped pattern, waffle pattern or similar configuration. Structural pattern 32 can be configured to reduce the overall mass and weight of splint device 10 by eliminating unnecessary material in each plate member 12, 14 and 16 while still providing structural strength and rigidity to each plate member 12, 14 and 16 and splint device 10 overall. According to one embodiment, the design of structural pattern 32 (such as a honeycomb pattern) can be constructed on plate member 12, 14 and 16 through injection molding technology (or other suitable manufacturing process) which can significantly reduce the cost of manufacturing. This construction can allow for the wall thickness of the mold forming the structural pattern 32 to be selectively adjusted to control the flow of forming material through the mold and maintain the proper shape of structural pattern 32 during cooling of plate member 12, 14 and 16.

Figure 3:
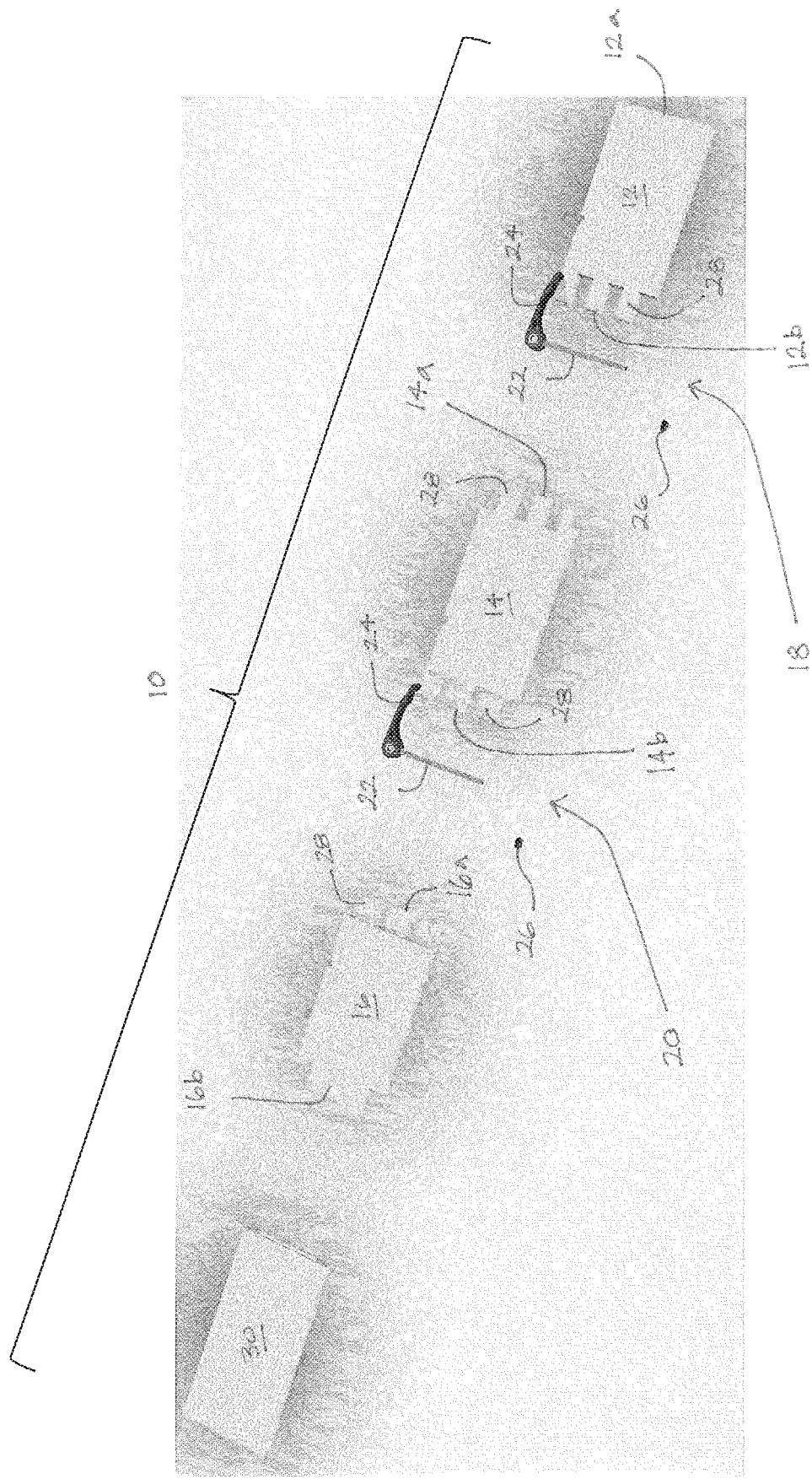
FIG. 3 is an exploded perspective view of the medical splint device of FIG. 1.
Figure 6:
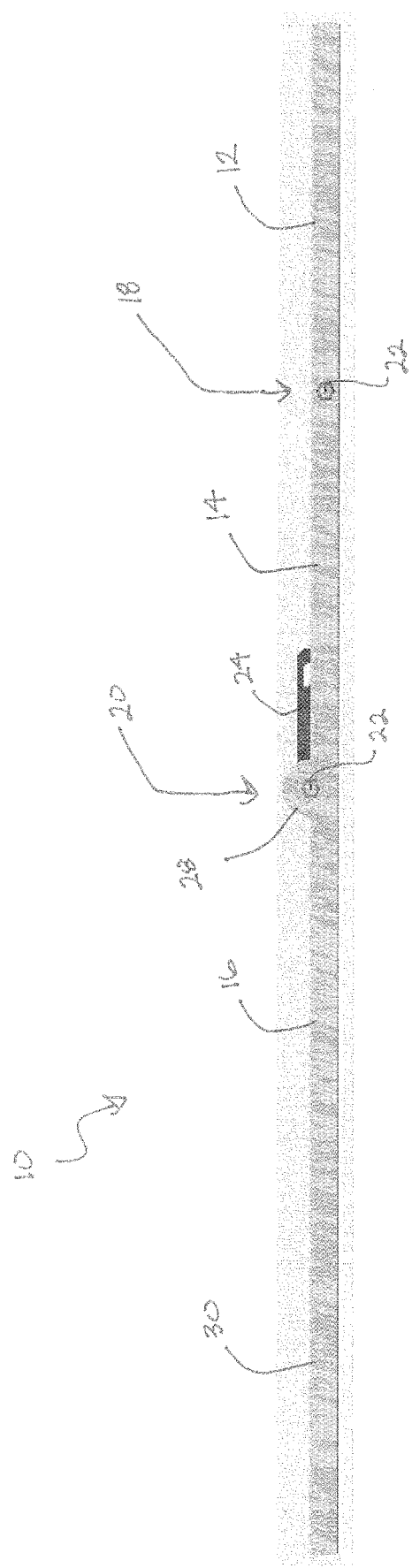
FIG. 6 is a rear elevation view of the medical splint device of FIG. 1.
Figure 7:
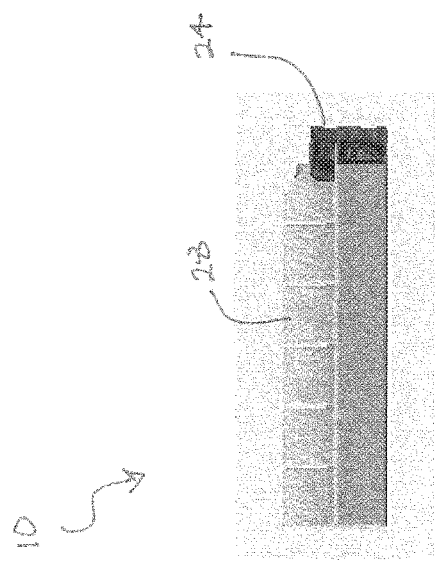
FIG. 7 is a side elevation view of the medical splint device of FIG. 1.

As best shown in FIGS. 3 and 4, first plate member 12 can include a free end 12a and a first connected end 12b. Similarly, second plate member 14 can include a first connected end 14a and a second connected end 14b, and third plate member can include a second connected end 16a and a free end 16b. As shown in FIGS. 3 and 4 (as well as FIGS. 1-2 and 5-7), the first connected ends 12b and 14a of the first and second plate members 12 and 14, respectively, can be connected together by a first hinged connection member 18, and similarly, the second connected ends 14b and 16a of the second and third plate members 14 and 16, respectively, can be connected together by a second hinged connection member 20. Hinged connection members 18 and 20 can be configured as any suitable type of hinge or pin connection to allow the plate members 12, 14 and 16 to be rotated relative to one another about an axis extending through the hinged connection members 18 and 20. As best shown in FIG. 3, according to one embodiment, hinged connection members 18 and 20 can each comprise a pin 22, a cam lever 24 and a fastener 26. However, it is recognized that any number of suitable pinned connection-type configurations can be suitably used in alternative embodiments. For example, FIGS. 16-22 show an alternative configuration of hinged connection members 18 and 20 where cam lever 24 is configured instead as a wheel knob 24.

Figure 10:
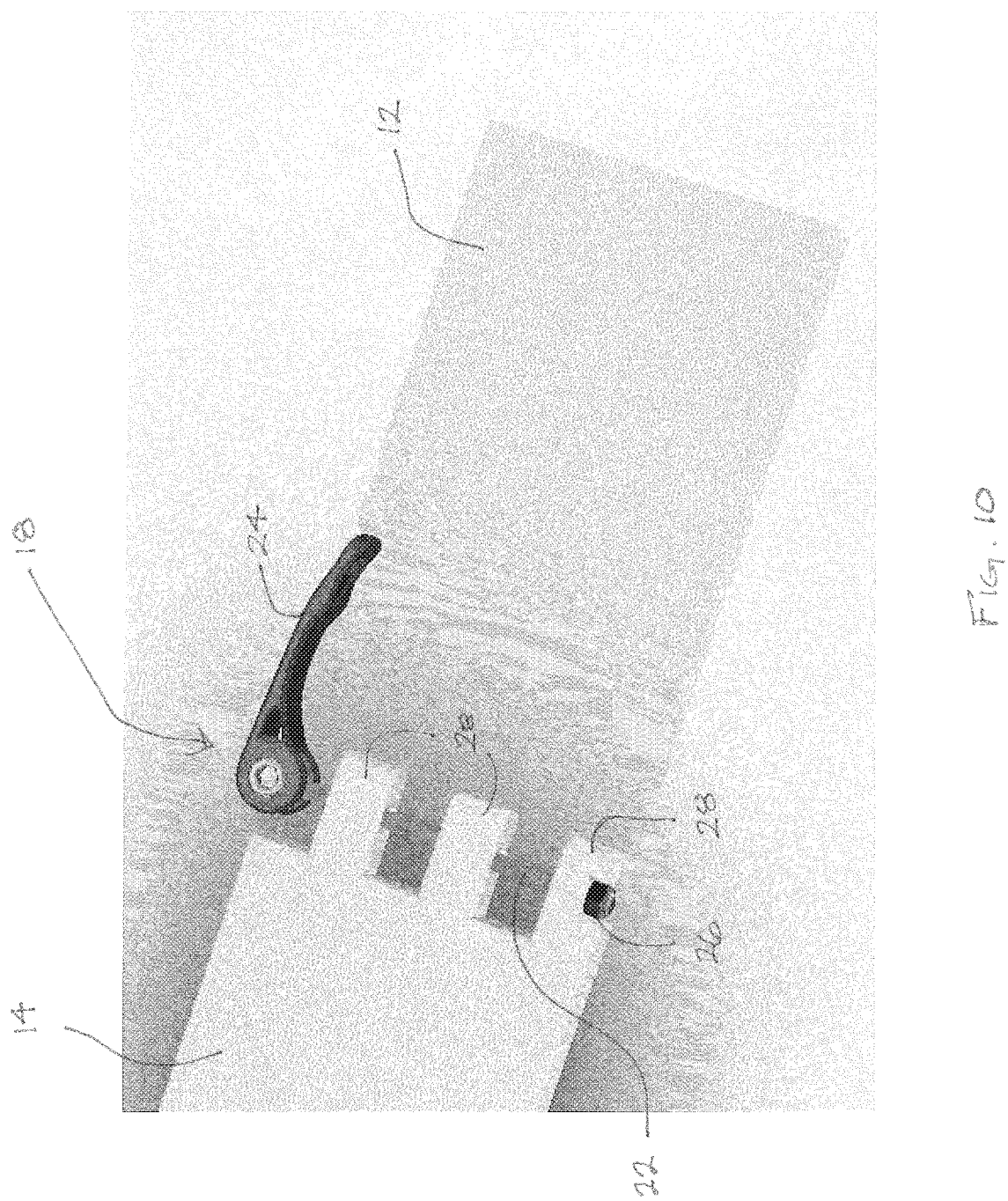
FIG. 10 is a partial schematic perspective view of the medical splint device of FIG. 1.

As best shown in FIGS. 3 and 10, the ends (12b and 14a, and 14b and 16a) of plate members 12, 14 and 16 adjacent to the hinged connection members 18 or 20 can be configured as a slotted or knuckled ends 28 to allow the plate members 12, 14 and 16 to be interlocked together and the pin 22 of the hinged connection to be inserted therethrough. FIG. 10 best illustrates the configuration of hinged connection members 18 and 20 and knuckled ends 28 of the plate members 12, 14 and 16 according to one embodiment of the present invention. As illustrated, the ends 28 are interwoven together and the pin 22 is inserted through each of the knuckles in the interwoven ends 28. The fastener 26 (which can be configured as any suitable type of fastener) is secured onto the end of the pin opposite the cam lever 24. The hinged connection members 18 and 20 allow for the plate members (12 and 14, or 14 and 16) to be rotated relative to one another in order to conform to the shape of a person's limb or a desired configuration for a person's limb. When the cam lever 24 (or wheel knob 24) is in a released position, the plate members 12 and 14 or 14 and 16 are unrestricted from rotational movement about the axis of the hinged connection member 18 or 20. The plate members 12 and 14 or 14 and 16 may accordingly be selectively positioned into a desired shape and configuration (such as the shape of a person's limb) and the cam lever 24 (or wheel knob 24) may then be placed into a secured position to lock the plate members 12 and 14 or 14 and 16 in an affixed position.

Figure 11:
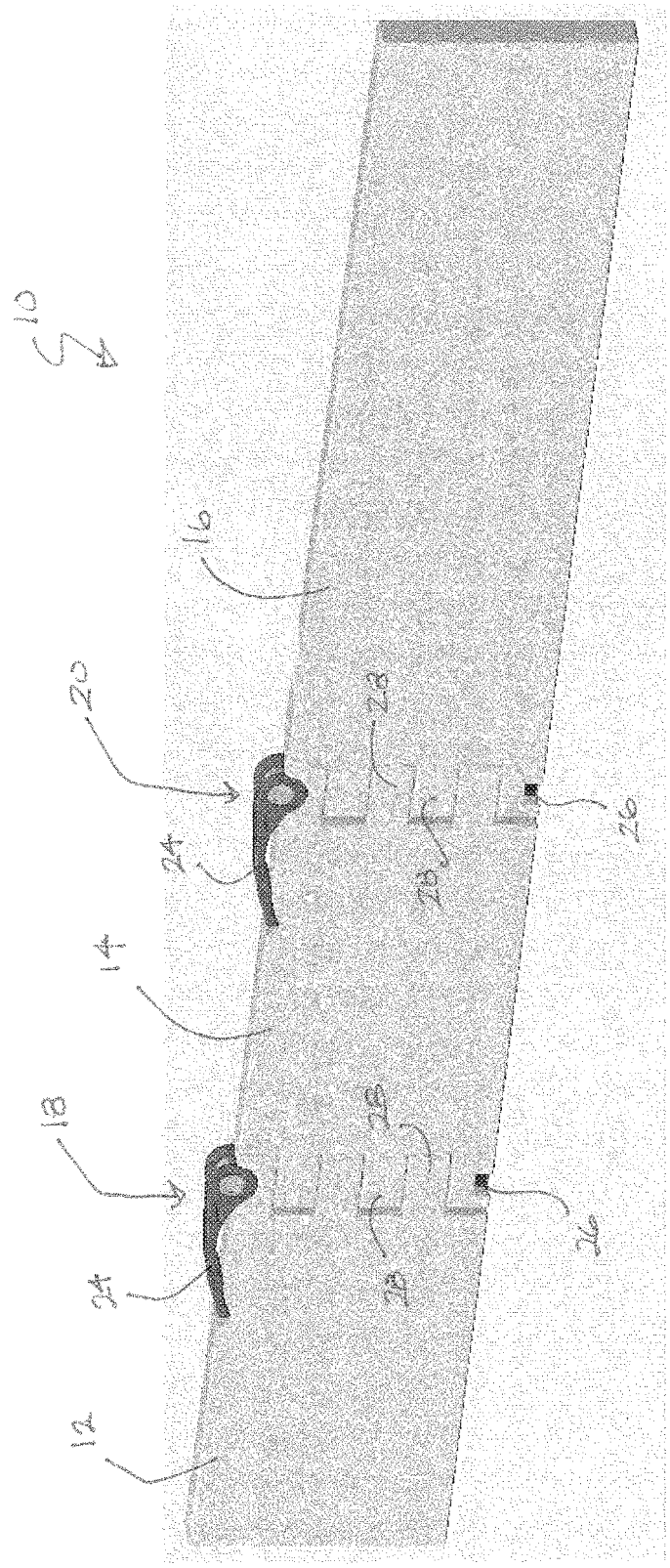
FIG. 11 is a perspective view of a medical splint device in accordance with a second embodiment of the present invention.
Figure 12:
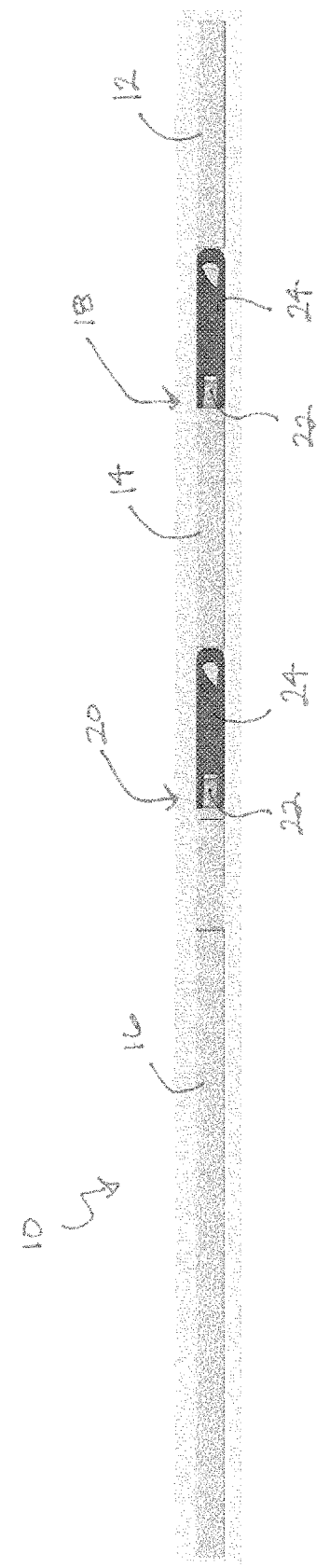
FIG. 12 is an elevation view of the medical splint device of FIG. 11.
Figure 13:
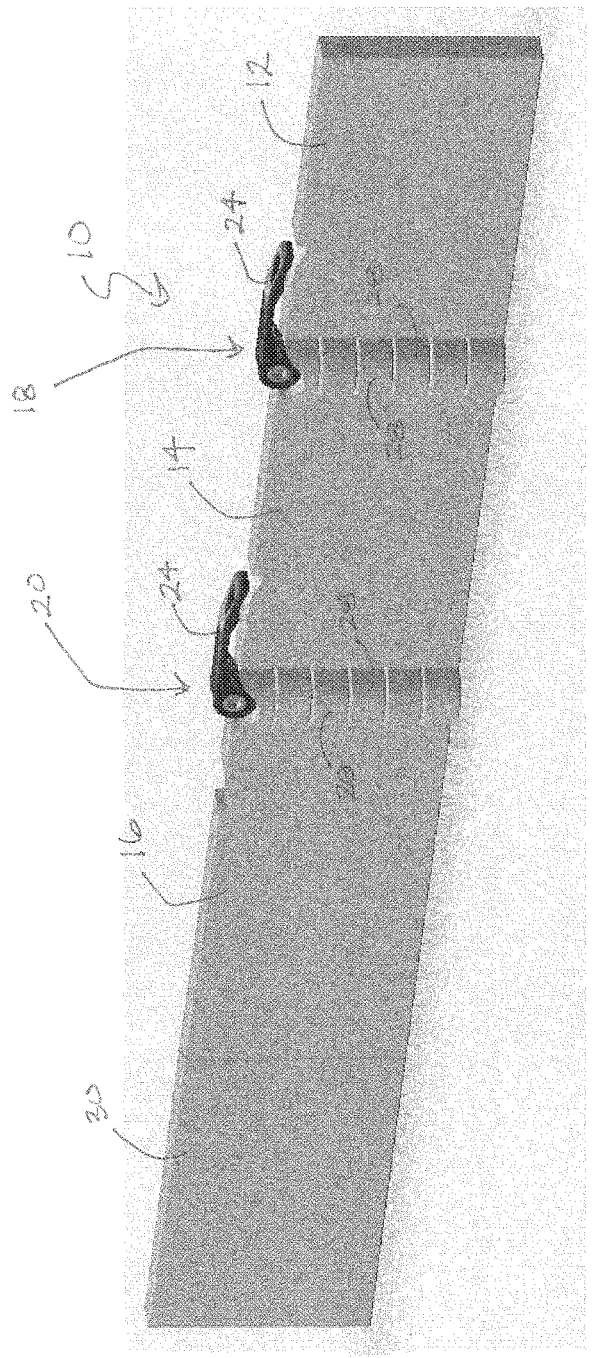
FIG. 13 is a perspective view of a medical splint device in accordance with a third embodiment of the present invention.
Figure 14:
FIG. 14 is a front elevation view of the medical splint device of FIG. 13.
Figure 15:
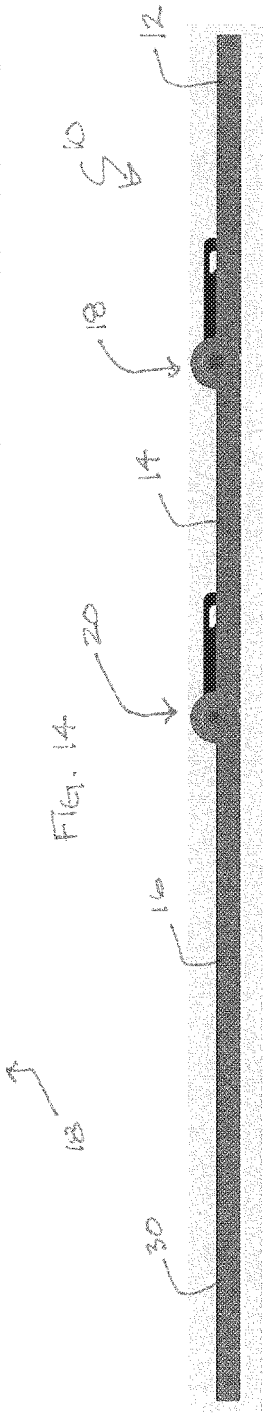
FIG. 15 is a rear elevation view of the medical splint device of FIG. 13.
Figure 10:
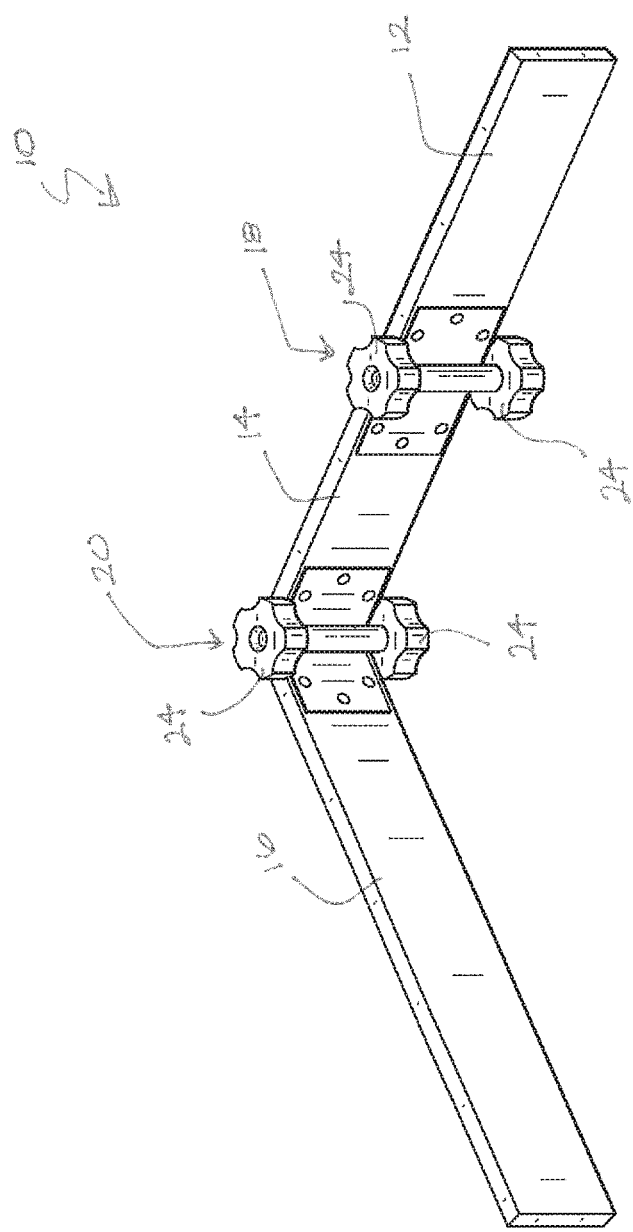

Depending on the particular embodiment of the splint device 10, the knuckled ends 28 of plate members 12, 14 and 16, which when paired together, formed part of the hinged connections 18 and 20, can be configured as flattened knuckles (see FIGS. 11-12), rounded knuckles (see FIGS. 13-15), a combination of flattened and rounded knuckles (see FIGS. 1-7), or any other suitable shape and configuration (not shown).

Figure 23:
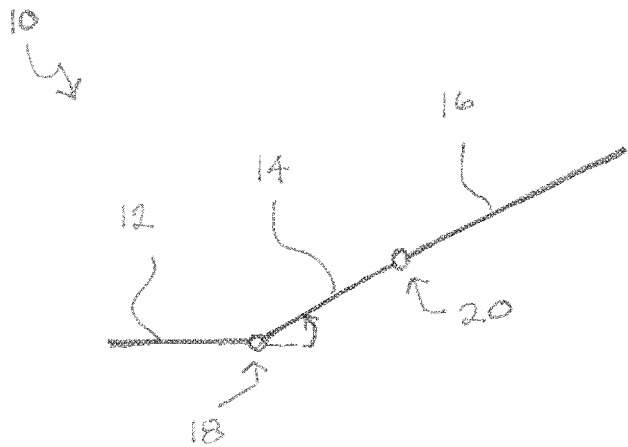
FIG. 23 is a schematic representation of a medical splint device in accordance with one embodiment of the present invention illustrating the selectively movable components of the device.
Figure 24:
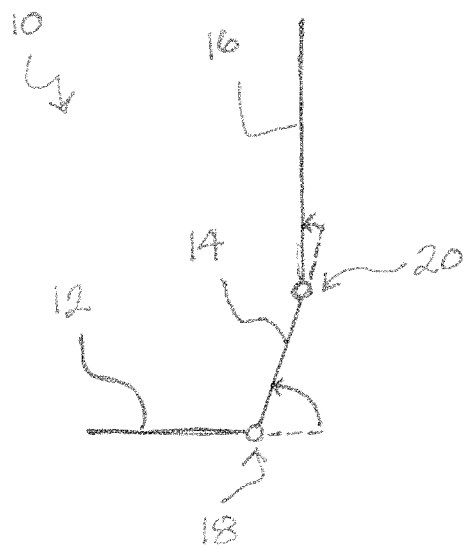
FIG. 24 is a schematic representation of a medical splint device in accordance with one embodiment of the present invention illustrating the selectively movable components of the device.
Figure 25:
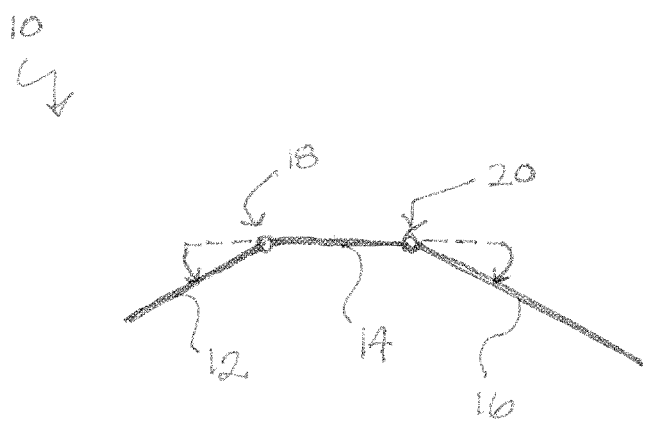
FIG. 25 is a schematic representation of a medical splint device in accordance with one embodiment of the present invention illustrating the selectively movable components of the device.

Turning to FIGS. 23-25, schematic representations of splint device 10 are shown according to one embodiment of the present invention to illustrate how splint device 10 can be positioned in effectively an unlimited number of configurations based on the selective rotation of plate members 12, 14 and 16 relative to one another via hinged connection members 18 and 20. The pinned connection of the hinged members 18 and 20 allow the each plate member 12, 14 and 16 to be rotated approximately 360 degrees relative to the adjacent plate member 12, 14 and 16. For example, FIG. 23 provides a schematic illustration where plate members 14 and 16 have been collectively rotated upward relative to plate member 12 about hinged connection 18. In FIG. 24, plate member 14 has been rotated relative to plate member 12 about hinged connection 18 and plate member 16 has been rotated relative to plate member 14 about hinged connection 20. In FIG. 25, both plate members 12 and 16 have been rotated relative to plate member 14 about hinged connections 18 and 20, respectively. As illustrated by the schematic representations of FIGS. 23-25, splint device 10 can be configured into almost any desired configuration, which can allow splint device 10 to be selectively configured for a particular application. For example, when used to stabilize a person's injured arm or leg for immobilization or otherwise, splint device 10 can be configured to more fully conform to the individual's limb by rotating plate members 12, 14 and 16 to conform to the shape of the limb and match the contours and bends at joints and along the length of the limb. Once the plate members 12, 14 and 16 are situated in the desired shape, the hinged members 18 and 20 can be locked in place through cam levers 24 (or locking knobs 24) to secure the splint device 10 and the injured arm or leg in a fixed position.

Further, as best illustrated in FIGS. 18-20, the hinged connections 18 and 20 of splint device 10 enable the device 10 to be folded into a compact shape when not in use to order to minimize its storage footprint. This can enable splint device 10 to be easily stored, transported and carried to improve its functionality.

Turning back to FIGS. 1-7, according to certain embodiments of the present invention, splint device 10 can optionally include an extension plate member 30. Extension plate member 30 can be configured and constructed in a similar manner as plate members 12, 14 and 16 as described above and can be secured to the free end of third plate member 16 opposite second hinged connection 20 as shown in FIGS. 1-7. In other embodiments (not shown), extension plate member 30 can also or alternatively be configured to extend from first plate member 12. As best shown in FIG. 3, according to one embodiment, extension plate member 30 can connect to third plate member 16 using a mortise and tenon-style connection. However, any other suitable connection types that provide sufficient rigidity can also be used in certain embodiments. Extension plate member 30 can be utilized when splint device 10 is required to span further distances than permitted by third plate member 16.

In addition, while the figures and the foregoing description illustrates and describes splint device 10 as having three plate members 12, 14 and 16 and two hinge connections 18 and 20, in alternative embodiments of the present invention (not shown), splint device 10 can alternatively include two plate members 12 and 14 and one hinge connection 18 connection plate members 18 and 20 together in accordance with the teachings above. In yet further embodiments, splint device 10 can also suitable utilize more than three plate members and additional hinge connections depending on the desired application and use of splint device 10.

As shown in FIGS. 27-30 and described above, one or more of plate members 12, 14 and 16 can include a structural pattern 32 provided on one or both surfaces the plate member 12, 14 and 16. According to one embodiment as shown in FIGS. 27-30, structural pattern 32 can be configured as a honeycomb-shaped or hexagonal-shaped pattern (it is also recognized that alternative patterns can also be suitably used in other embodiments) defined into one surface of the plate member 12, 14 and 16 to form plurality of void spaces 34. As described above, structural pattern 32 can be used to reduce the overall mass and weight of splint device 10 while maintaining sufficient structural strength and rigidity to prevent undesirable twisting and flexing of plate members 12, 14 and 16. In addition, according to one embodiment, void spaces 34 can be configured as sockets or receptacles 34 that can allow accessories to be easily attached to splint device 10. In such a configuration, each void space (i.e., socket) 34 can be shaped to substantially conform to a connection component on an associated accessory, such as a strap or other part. A user can insert the connection component into the socket 34 and the frictional fit provided between the socket 34 and connection component secures the corresponding accessory to splint device 10.

As described herein, splint device 10 can be designed and configured to selectively secure a person's arm, leg, other appendage or appendages, or entire or portions of a body, in a specific fixed position. Splint device 10 can also be utilized in a variety of different applications. For example, splint device 10 can be used to secure an injured limb in a fixed position following a medical injury, during rehabilitation therapy, or during transport of a patient. In addition, splint device 10 can be utilized as a protective measure for patients with weakened muscles or bones (e.g., osteogenesis imperfecta). Such an application may be particularly useful in connection with persons involved in space travel and missions where long durations away from Earth's gravity occur and a person is required to spend an extended period of time in a moderately fixed position. In such instances, long duration of exposure to microgravity can cause muscle atrophy and bone demineralization resulting in weaker muscles or bones, and splint device 10 may be advantageously used to support a person's limbs or extremities while being re-acclimated to Earth's gravity.

Splint device 10 can include padding and can be held in place with straps, bandages or other means to custom fit splint device 10 to a particular patient. The adjustability of splint device 10 as described herein can allow splint device 10 to secure a limb in a secure, selective position where the joint is placed in a position of comfort or placed in a position desirable for recovery, rehabilitation or a medical procedure.

From the foregoing, it will be seen that this invention is one well adapted to attain all the ends and objects hereinabove set forth together with other advantages which are obvious and which are inherent to the structure. It will be understood that certain features and sub combinations are of utility and may be employed without reference to other features and sub combinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A splint device comprising:
    a first plate member having a free end and a first connected end;
    a second plate member having a first connected end and a second connected end; and
    a first hinged connection member positioned between said first connected ends of said first plate member and said second plate member, said first hinged connection member configured to connect said first and second plate members together;
wherein said first hinged connection member comprises a cam lever, a pin and a fastener and said first and second plate members are selectively rotatable relative to one another when the cam lever is in an open position, and
wherein said first and second plate members are not selectively rotatable relative to one another when the cam lever is in a closed position.

2. A splint device, comprising:
    a first plate member having a free end and a first connected end;
    a second plate member having a first connected end and a second connected end; and
    a first hinged connection member positioned between said first connected ends of said first plate member and said second plate member, said first hinged connection member configured to connect said first and second plate members together;
wherein said first hinged connection member allows said first and second plate members to be selectively rotated relative to one another, and
wherein said first hinged connection member comprises a pin, a fastener, and a cam lever.

3. The splint device of claim 2, wherein said first connected ends include a plurality of knuckles to allow said plate members to be interconnected together at said first hinged connection member.

4. The splint device of claim 2, wherein said connected ends of plate members each include a slot configured to allow said pin to be inserted therethrough.

5. The splint device of claim 2, wherein said first plate member may be rotated relative to said second plate member by at least 180-degrees about an axis extending longitudinally through said first hinged connection member.

6. The splint device of claim 2, wherein said plate members are formed by a 3-dimensional printing process.

7. The splint device of claim 2, wherein said plate members are formed by injection molding.

8. The splint device of claim 2, further comprising an extension plate member.

9. The splint device of claim 2, wherein said cam lever, pin and fastener of said first hinged connection member selectively prevent rotation of said first and second plate members when the cam lever is in a closed position, and wherein said first hinged connection member may be selectively adjusted to a released position when the cam lever is in an open secured position.

10. The splint device of claim 2 comprising a third plate member having a free end and a second connected end, and a second hinged connection member positioned between said second connected ends of said second and said third plate members, said second hinged connection member configured to connect said second and third plate members together.

11. The splint device of claim 10, wherein said third plate member may be rotated relative to said second plate member by at least 180-degrees about an axis extending longitudinally through said second hinged connection member.

12. The splint device of claim 10, further comprising an extension plate, said extension plate member being fixedly connected to said free end of said third plate member.

13. The splint device of claim 10, wherein said pin, fastener and cam lever selectively prevents rotation of said plate members connected together by said hinged connection member when the cam lever is in a closed position,
    wherein said first and second hinged connection members may be selectively adjusted between a released position and a secured position.

14. The splint device of claim 13, wherein said first plate member may be rotated relative to said second plate member by at least 180-degrees about an axis extending longitudinally through said first hinged connection member, or said second plate member may be rotated relative to said third plate member by at least 180-degrees about an axis extending longitudinally through said second hinged connection member.

15. The splint device of claim 10, wherein at least one of said first, second or third plate member includes a surface having a structural pattern defined into said surface.

16. The splint device of claim 15, wherein said structural pattern includes a plurality of void spaces defined into said surface, wherein at least one void space of said plurality of void spaces is configured as a socket for receiving an accessory to be attached to said splint device.

17. The splint device of claim 16, wherein said surface having said structural pattern defined thereon is a bottom surface of said first, second or third plate member or a combination of said first, second or third plate members.

18. The splint device of claim 2, wherein said first end of said first plate member and said first end of said second plate member include a plurality of knuckles to allow said first and second plate members to be interconnected together at said first hinged connection member, and wherein said first end of said third plate member and said second end of said second plate member include a plurality of knuckles to allow said second and third plate members to be interconnected together at said second hinged connection member.

* * * * *